(12) United States Patent
Johans et al.

(10) Patent No.: US 7,281,416 B2
(45) Date of Patent: Oct. 16, 2007

(54) METHOD FOR SURFACE TENSION MEASUREMENT

(75) Inventors: Christoffer Johans, Espoo (FI); Pekka Suomalainen, Tuusula (FI); Paavo Kinnunen, Espoo (FI)

(73) Assignee: Kibron Inc. Oy, Helsinki (FI)

( * ) Notice: Subject to any disclaimer, the term of this patent is extended or adjusted under 35 U.S.C. 154(b) by 36 days.

(21) Appl. No.: 10/527,085

(22) PCT Filed: Sep. 15, 2003

(86) PCT No.: PCT/FI03/00671

§ 371 (c)(1), (2), (4) Date: Nov. 8, 2005

(87) PCT Pub. No.: WO2004/025277

PCT Pub. Date: Mar. 25, 2004

(65) Prior Publication Data

US 2006/0123893 A1     Jun. 15, 2006

(30) Foreign Application Priority Data

Sep. 13, 2002   (FI) .................................. 20021643

(51) Int. Cl.
*G01N 13/00* (2006.01)
(52) U.S. Cl. ..................................... 73/64.49; 73/64.48
(58) Field of Classification Search ............... 73/64.48, 73/64.49, 64.51, 64.52, 53.01
See application file for complete search history.

(56) References Cited

U.S. PATENT DOCUMENTS

| 4,735,778 A | * | 4/1988 | Maruyama et al. | ......... 422/102 |
| 5,802,816 A | * | 9/1998 | Dietzel | ....................... 53/453 |
| 6,857,309 B2 | * | 2/2005 | Mansky | ..................... 73/64.49 |

FOREIGN PATENT DOCUMENTS

WO       WO 99/49974 A1     10/1999

\* cited by examiner

*Primary Examiner*—Hezron Williams
*Assistant Examiner*—Rodney Frank
(74) *Attorney, Agent, or Firm*—Kratz, Quintos & Hanson, LLP

(57) ABSTRACT

The present invention is directed to a method for measuring the surface tension of a sample comprising providing a well plate, containing at least one well defined by well walls and an opening and forming a space for receiving the sample to be tested, bringing a probe in contact with the surface of the sample in the well, and measuring the force applied to the probe by the sample, characterized in that the walls of the well are inclined with respect to the plane defined by the opening of the well so that the cross section of the well is decreasing in the direction from the opening of the well towards the bottom of the same, so as provide a geometry resulting in a flat or convex shape of the meniscus of the sample when in the well and that at least the surface of the wall of the well facing the sample space comprises an antistatic material, and providing means for dissipating static electricity from the well. The invention also concerns a well plate for use in the method.

24 Claims, 3 Drawing Sheets

A-A

METHOD FOR SURFACE TENSION MEASUREMENT

FIELD OF THE INVENTION

The present invention generally relates to a method for measuring surface tension. Specifically the invention concerns the design of a well plate intended for surface tension measurement by using a probe to be brought into contact with the surface of a sample in a well in the well plate. The invention can be used for measuring the surface chemical properties of a substance, such as a drug.

BACKGROUND OF THE INVENTION

The amphiphilicity and surface activity properties of a substance, such as of a drug, correlate to its adsorption in the gastro-intestinal tract, to its distribution in the tissues and especially to its blood-brain barrier (BBB) permeability, liver metabolism and urinary excretion, that is to its so-called ADME properties. Amphiphilicity and detergent properties have conventionally been determined by measuring the effect of the substance on the surface tension of water. Another conventionally used method for estimating ADME properties is to determine the partition coefficient (log P) of the substance in octanol/water.

When an amphiphilic substance is added to an aqueous solution, the substance partitions into the air/water interface, causing a decrease in the surface tension (increase in the surface pressure). Surface tension can be measured for example by measuring the force applied to a probe in the air/water interface. Such a probe can be in the form of a thin platinum plate such as a Wilhelmy plate, which is placed in the air/water interface. An alternative construction for the probe is in the form of a small diameter metal wire.

A change in surface tension is evidenced as a change in the amount of liquid adhered to the probe. When the surface tension of the liquid decreases, the amount adhered to the probe decreases linearly, and vice versa. The liquid adhered exerts a vertical force on the probe, which can be detected using a microbalance.

Generally, surface tension measurement techniques require large reagent volumes and long experimental times. The huge increase in screening of new drug candidates requires, however, fast and reliable techniques applicable over a wide surface tension range. Additionally, for economic reasons, miniaturization of the reagent volumes is especially desirable for expensive substances, such as drug candidates.

SUMMARY OF THE INVENTION

An object of the invention is a method for measuring the surface tension of a sample comprising providing a well plate containing at least one well defined by well walls, the walls defining a well opening and the walls of the well forming a space for receiving the sample to be tested, bringing a probe in contact with the surface of the sample in the well, and measuring the force applied to the probe by the sample. The method is characterized in that the walls of the well are inclined with respect to the plane defined by the opening of the well so that the cross section of the well is decreasing in the direction from the opening of the well towards the bottom of the same, so as to provide a geometry resulting in a flat or convex shape of the meniscus of the sample in the well and that at least the surface of the wall of the well facing the sample space comprises an antistatic material, as well as providing means for dissipating static electricity from the well.

The antistatic material is needed to lead away or discharge possible static electricity that may occur in the sample wells, which could otherwise disturb the measurement. The means for enabling a dissipation of possible antistatic electricity from the sample wells can be provided by selected parts of the well plate comprising or being coated with an antistatic material. Thus the means can comprise providing the whole well plate, or the whole surface of the well plate, with an antistatic material and the well plate be grounded to lead away possible charges from the sample wells. In addition to the sample wells or the surface thereof, e.g. in the form of a coating, specific parts or areas of the well plate associated or connected thereto can form regions or paths comprising antistatic material communicating with the well and through which charges can be conducted away or discharged. Thus the term 'selected parts' of the well plate as used in the invention is intended to comprise, besides parts of the well, also the whole well plate, including e.g. a layer, such as a surface layer of such selected parts.

The cross section mentioned above refers to a cross section of the well parallel to the plane defined by or containing the opening of the well. This also means that the diameter of such a cross section of the well decreases in a direction from the opening to the bottom of the well. Preferably the well is shaped as a cone or a truncated cone. The invention also concerns a well plate suitable for the method described above. The well plate is defined as described in the claims.

According to an embodiment of the invention the well plate is prepared from an antistatic, i.e. conductive or dissipative material to prevent interference of static electricity during the measurement.

The sample to be tested is preferably an aqueous solution of a substance, such as a drug, the ADME-properties of which are to be determined.

DETAILED DESCRIPTION OF THE INVENTION

Trials leading to the invention have shown that in order to get reliable and reproducible results when measuring the surface tension of a sample in a small well, it is essential that a convex or flat meniscus is formed by the sample. If, in contrast, a concave meniscus is formed by the sample, a probe inserted in the sample will be drawn to the side of the well and the measuring result will be unreliable. According to the invention this problem can be solved by using, in the method, a well shape that provides a convex or flat meniscus to the sample. A convex or flat shape of the meniscus will maintain the probe in the center of the sample surface. This in turn gives an accurate measurement value even using small volumes of sample fluid as in the case e.g. when using said measurements for drug solutions.

According to the invention a well with inclined converging walls as defined will result in a convex or flat shape of the meniscus of the sample, regardless of the sample volume and the surface tension of the solution. The contact angle $\alpha$ between the sample fluid and the walls of the well is an intrinsic quantity that is defined by the properties of the well-fluid, well-air and fluid-air interfaces. According to the invention, if the top angle of the well, i.e. the angle between the walls or the extension of the walls of the well, is designated $\beta$, then in order to provide a convex or flat meniscus, the top angle $\beta$ must be smaller than or equal to 180−α, or in other words, the contact angle of the sample, α, is 90°−β/2≦α<180°. The degree of inclination of the walls can vary, but testing has shown that the top angle β formed between the walls or the extension of the walls should lie in the interval between 30° and 150°, preferably 70° to 90°.

According to an embodiment of the invention, the material used for the wells and the well plate should be antistatic. Presence of static electricity affects the measurements resulting in distorted measurement values. It is especially essential to avoid the presence of static electricity or electrical charges while measuring surface tension of small volume samples, where the distances between the probe and the walls of the cuvette are short. In such measurements even small electrical charges can lead to significant measurement errors. Since aqueous sample solutions are generally used, the material is preferably hydrophobic to further facilitate the formation of the convex shape of the meniscus of the sample. To obtain antistatic qualities of the material, conductive or inherently dissipative materials can be used. Such a material can be a polyolefin, preferably polypropylene with an addition of carbon or metal particles. The carbon or metal should be integrated in the material of the well plate to give the best results. The material used should also be as pure as possible, without any traces of e.g. softeners and slipping agents that may dissolve in the fluid. At least the surface of the wall facing the sample space should be lined with the said hydrophobic material. The materials described above are known and are commonly used to avoid static electricity in various devices.

According to an embodiment of the invention the height of the walls of the well plate have to be at least 1 mm deep for the probe to fit in to the well. The depth of a well is typically appr. 3 mm. The probe is typically lowered 1 mm into the surface of the sample in the well during measurement and a contact between the probe and the well itself would naturally result in incorrect measurement values.

A geometry favoring a small distance between the sample surface and the upper surface of the well, i.e. the opening of the well, is preferred to reduce the necessary movement of the probe. The use of a well plate where the edges of the wells extend vertically above the sample space of the well is of course possible, but results in an increased movement of the probe, which is not advisable. Another problem with extending vertical walls is that an amount of sample fluid that fills the well to a level up to the vertical part may result in a concave shape of the meniscus of the sample fluid, which in turn leads to incorrect measurement values, as stated above.

BRIEF DESCRIPTION OF THE DRAWINGS

In the enclosed drawings.

THE INVENTION WILL BE DEMONSTRATED BY THE FOLLOWING EXAMPLE

The surface tension of water was measured on a MultiPi HTS instrument (Kibron Inc.) by the Du Nuoy ring technique on four different plate types. This experiment demonstrates that both the material as well and shape are important for accurate surface tension measurements. The materials in the plates were polypropylene, conductive polypropylene, aluminum and a standard commercially available polystyrene 96-well plate (Nunc). In the two former the geometry of the well has been designed to give a convex meniscus shape. These two differ only in their conductivity. The shape of the aluminum plate has not been optimized and a concave meniscus shape is obtained.

Figure 1:
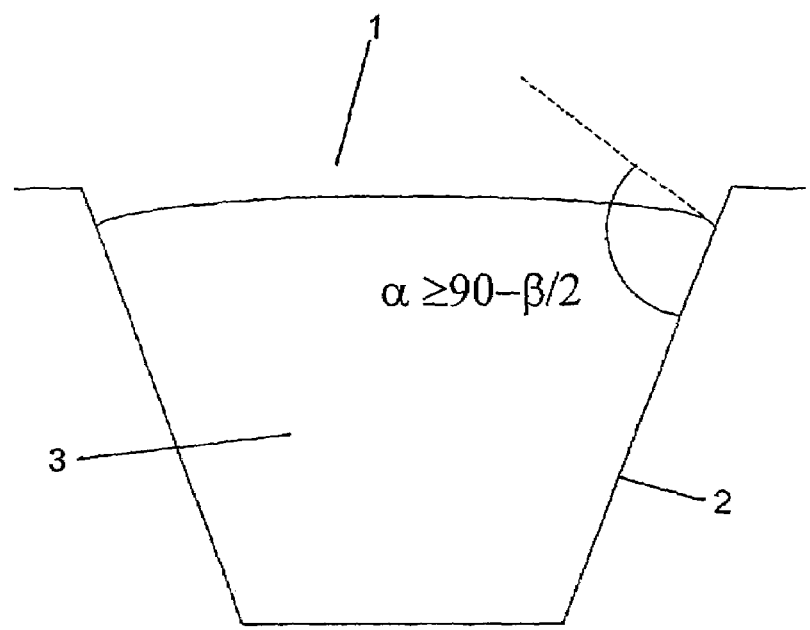
FIG. 1 shows a well 1 in accordance with the invention and the contact angle α formed by a sample 3 in the well. The limits within which α can vary are: 90°−β/2≦α<180°, where β is the top angle between the walls 2 or the extension of the walls.
Figure 2:
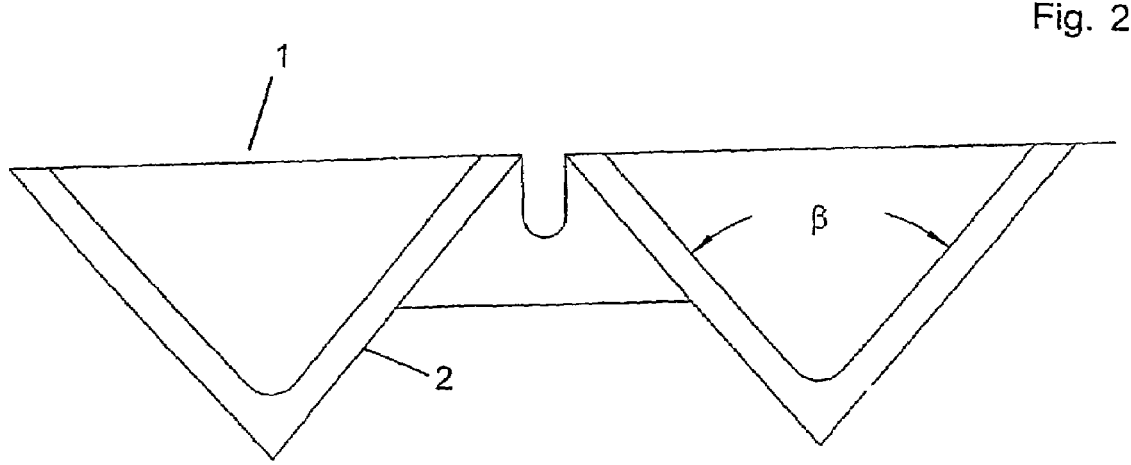
FIG. 2 shows a cross-section of two neighboring wells 1 of a well plate according to a preferred embodiment of the invention. The top angle β is indicated.
Figure 3A:
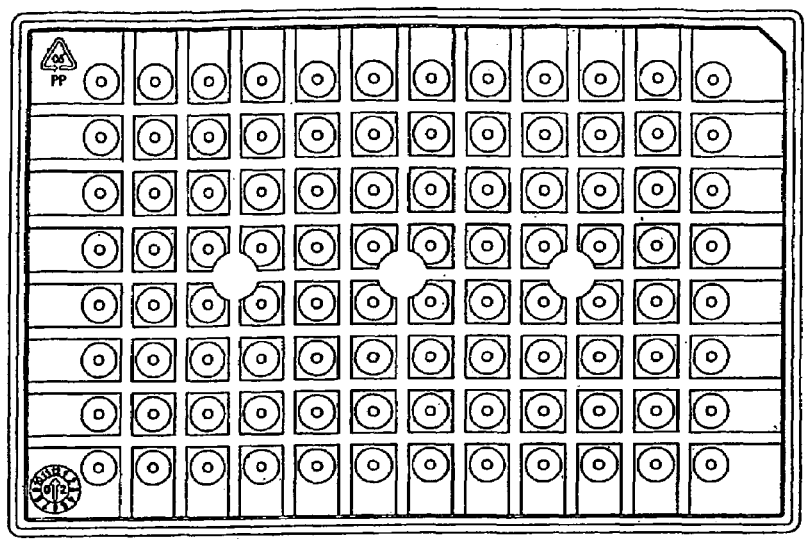
FIG. 3a shows the well plate of a preferred embodiment from below, FIG. 3b the cross section A-A of the same and FIG. 3c the well plate from above. In this preferred embodiment of the invention the well plate has the standard footprint and plate size facilitating the implementation of standard laboratory robotics.
Figure 3B:
Figure 3C:
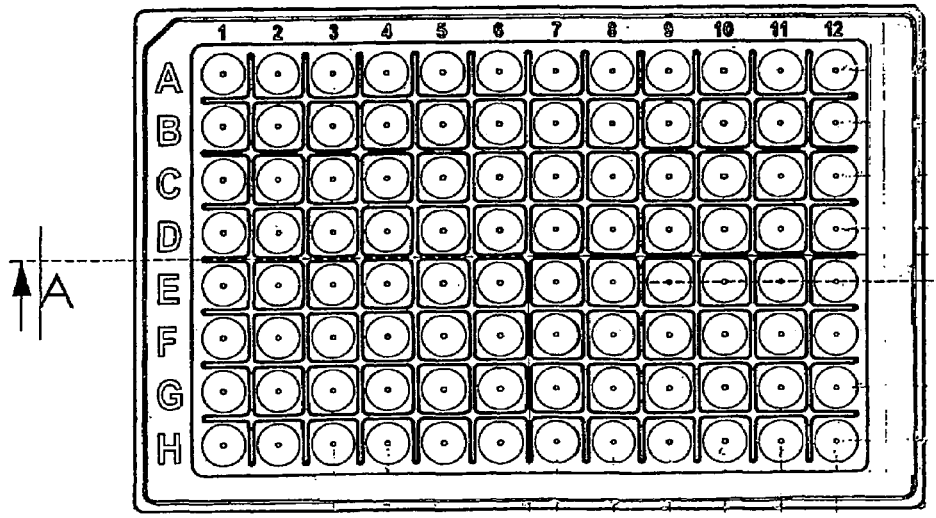
Figure 4:
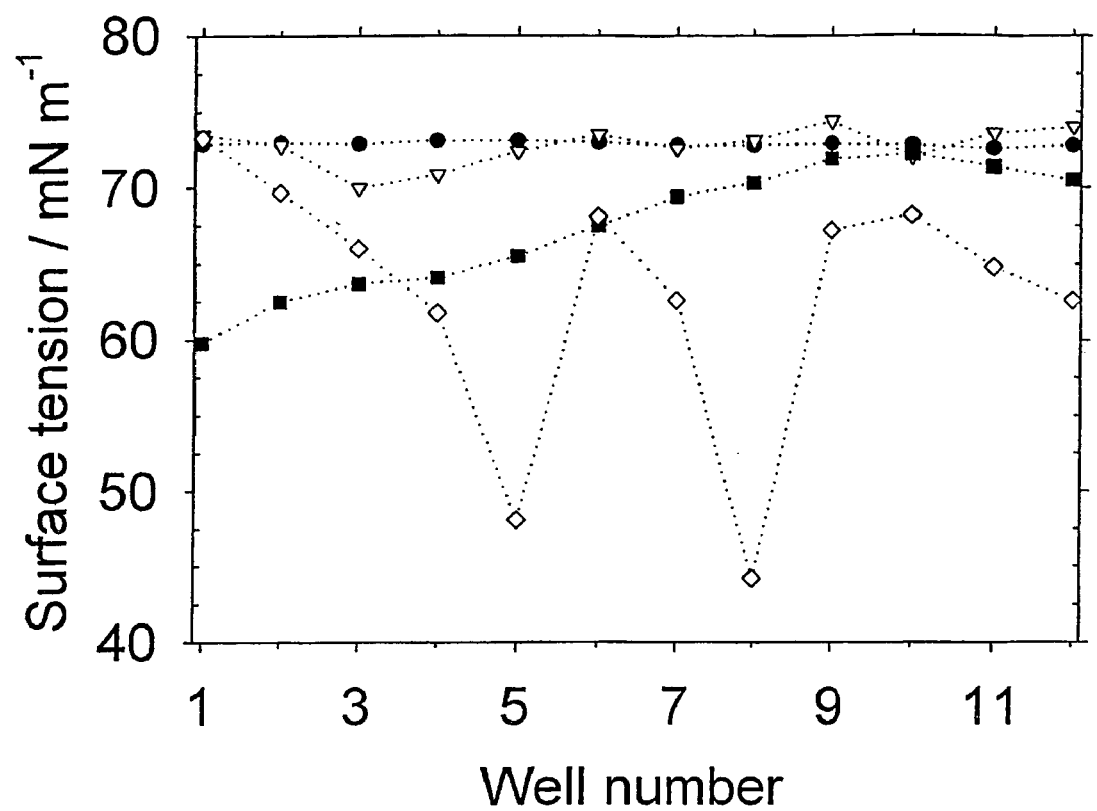
FIG. 4 shows in graphic form the surface pressure measured in four different well plates: conductive propylene (●), propylene (■), aluminum (▽) and a standard 96-well plate (◇).

The results of the experiment are shown in FIG. 1. The conductive polypropylene plate (●) shows correct values throughout the series of wells. The polypropylene plate (■) suffers from static electricity that is apparent, especially in the beginning of the well series, as too low and variable surface tension values. The decreasing error is due to the discharging of the static electricity through the probes. The experimental results obtained with the aluminum plate (▽) vary randomly depending on how the meniscus shape is distorting the measurement probe. The standard 96-well plate (◇) suffers from both static electricity as well as poor well shape.

The invention claimed is:

1. A method for measuring the surface tension of a sample, comprising the steps of:
providing a well plate containing at least one well defined by well walls defining a well opening and the walls of the well forming a space for receiving the sample to be tested;
bringing a probe in contact with the surface of the sample in the well;
measuring the force applied to the probe by the sample, wherein the walls of the well are inclined with respect to the plane defined by the opening of the well so that the cross section of the well is decreasing in the direction from the opening of the well towards the bottom of the same, so as provide a geometry resulting in a flat or convex shape of the meniscus of the sample in the well and that at least the surface of the wall of the well facing the sample space comprises an antistatic material; and
providing means for dissipating static electricity from the well.

2. The method according to claim 1, wherein the well has the shape of a cone or a truncated cone.

3. The method according to claim 2, wherein the top angle β of the cone is between 30° to 150°.

4. The method according to claim 1, wherein the means for dissipating static electricity from the well are provided by selected parts of the well plate comprising an antistatic material.

5. The method according to claim 1 or 4, wherein the entire well plate is made of an antistatic material.

6. The method according to claim 1, wherein the antistatic material is a hydrophobic material.

7. The method according to claim 6, wherein the hydrophobic material used is a conductive, inherently dissipative material.

8. The method according to claim 1, wherein the surface tension is measured from an aqueous solution.

9. The method according to claim 8, wherein the sample is an aqueous solution of a drug and is used for testing ADME-properties of the drug.

10. A well plate containing at least one well defined by well walls and an opening and forming a space for receiving a sample to be tested, wherein the walls of the well are inclined with respect to the plane defined by the opening of the well so that the cross section of the well is decreasing in the direction from the opening of the well towards the bottom of the same, so as to provide a geometry resulting in a flat or convex shape of the meniscus of the sample when in the well and that at least the surface of the wall of the well facing the sample space comprises an antistatic material, and comprising means for dissipating static electricity from the well, wherein the well has the shape of a cone or a truncated cone, and wherein the ton angle β of the cone is between 30° to 150°.

11. The well plate according to claim 10, wherein the means for dissipating static electricity from the well are provided by selected parts of the well plate comprising an antistatic material.

12. The well plate according to claim 10, wherein the entire well plate is made of an antistatic material.

13. The well plate according to claim 10, wherein the antistatic material is a hydrophobic material.

14. The well plate according to claim 13, wherein the hydrophobic material used is a conductive, inherently dissipative material.

15. The method according to claim 2, wherein the top angle β of the cone is between 70° to 90°.

16. The method according to claim 1, wherein the means for dissipating static electricity from the well are provided by selected parts of the well plate being coated with an antistatic material.

17. The method according to claim 1 or 4, wherein the entire well plate is coated with an antistatic material.

18. The method according to claim 6, wherein the hydrophobic material is a polyolefin.

19. The method according to claim 7, wherein the conductive, inherently dissipative material is polypropylene of high purity comprising carbon or metal particles.

20. The well plate according to claim 10, wherein the top angle β of the cone is between 70° to 90°.

21. The well plate according to claim 10, wherein the means for dissipating static electricity from the well are provided by selected parts of the well plate being coated with an antistatic material.

22. The well plate according to claim 10, wherein the entire well plate is coated with an antistatic material.

23. The well plate according to claim 13, wherein the hydrophobic material is a polyolefin.

24. The well plate according to claim 14, wherein the conductive, inherently dissipative material is polypropylene of high purity comprising carbon or metal particles.

* * * * *